United States Patent [19]

Huebner

[11] 4,054,570
[45] Oct. 18, 1977

[54] 4-PIPERIDINOBUTYROPHENONES

[75] Inventor: Charles Ferdinand Huebner, Chatham, N.J.

[73] Assignee: Ciba-Geigy Corporation, Ardsley, N.Y.

[21] Appl. No.: 556,599

[22] Filed: Mar. 10, 1975

Related U.S. Application Data

[63] Continuation-in-part of Ser. No. 407,737, Oct. 18, 1973, Pat. No. 3,992,546.

[51] Int. Cl.$^2$ .................. C07D 211/22; C07D 211/32
[52] U.S. Cl. ................................ 260/293.8; 424/263; 260/297 R
[58] Field of Search .................................. 260/293.8

[56] References Cited

U.S. PATENT DOCUMENTS

| | | | |
|---|---|---|---|
| 3,462,444 | 8/1969 | Beckett et al. | 260/293.8 |
| 3,806,526 | 4/1974 | Carr et al. | 260/293.8 |
| 3,888,867 | 6/1975 | Carr | 260/293.8 |

*Primary Examiner*—Henry R. Jiles
*Assistant Examiner*—R. W. Ramsuer
*Attorney, Agent, or Firm*—Theodore O. Groeger

[57] ABSTRACT

4'-Fluoro-4-[4-(α-hydroxy-aralkyl)-piperidino]-butyrophenones, preferably those of the formula

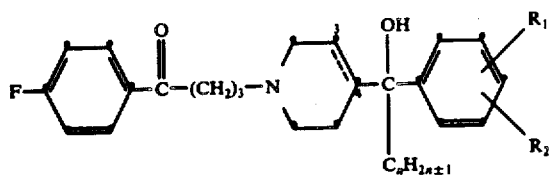

$n = 1$ to 7; $R_1, R_2 =$ H, alkyl, alkoxy, halo or $CF_3$; the 3,4-dehydro derivatives and salts thereof are neuroleptic agents.

3 Claims, No Drawings

4-PIPERIDINOBUTYROPHENONES

CROSS-REFERENCE TO RELATED APPLICATION

This is a continuation-in-part of application Ser. No. 407,737, filed Oct. 18, 1973 now U.S. Pat. No. 3,992,546.

BACKGROUND OF THE INVENTION

In Belgian Pat. No. 775,593, secondary alcohols of the above formula are disclosed, wherein $n = 0$, which compounds are claimed as tranquilizers. The compounds of the invention above and hereinafter described, unexpectedly do not show tranquilizing effects to a useful degree, but exhibit mainly neuroleptic activity.

SUMMARY OF INVENTION

The present invention concerns and has for its object the provision of compounds corresponding to Formula I

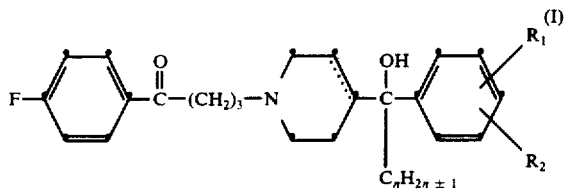

wherein $n$ is an integer from 1 to 7, each of $R_1$ and $R_2$ is hydrogen, lower alkyl, lower alkoxy, halo or trifluoromethyl, the 3,4-dehydro derivative or a therapeutically acceptable acid addition salt thereof, of corresponding pharmaceutical compositions and of methods for the preparation and application of these products, which are useful neuroleptic agents.

DESCRIPTION OF THE PREFERRED EMBODIMENTS

The radical $C_nH_{2n+1}$, is either alkyl, alkenyl, cycloalkyl or cycloalkyl-alkyl of 1–7 carbon atoms, e.g. methyl, ethyl, n- or i-propyl or -butyl, straight or branched pentyl, hexyl or heptyl; allyl or methallyl; cyclopropyl, cyclobutyl, cyclopentyl, cyclohexyl or cycloheptyl; cyclopropyl-methyl, cyclobutyl-ethyl, cyclopentyl-methyl or cyclohexyl-methyl. Most preferred are alkyl radicals $C_nH_{2n+1}$, wherein $n$ is an integer from 1 to 4, expecially methyl.

Of the radicals $R_1$ and $R_2$ both represent preferably hydrogen, but one or both are also lower alkyl, e.g., that mentioned above; lower alkoxy, e.g., methoxy, ethoxy, n or i-propoxy or butoxy; halo, e.g., fluoro, chloro or bromo; or trifluoromethyl. The term "lower" referred to above or hereinafter in connection with organic radicals or compounds, respectively, defines each with up to 7, preferably up to 4, carbon atoms.

Salts of the compounds of Formula 1 are preferably therapeutically acceptable acid addition salts derived, for example, from the inorganic or organic acids listed below.

The compounds of the invention exhibit valuable pharmacological properties. Besides antihypertensive activity, they show especially neuroleptic effects. This can be demonstrated in animal tests, using advantageously mammals such as mice, rats, and especially monkeys, as test objects. Said compounds are applied either enterally or parentally, e.g., orally, subcutaneously, intraperitoneally or intravenously, for example, within gelatin capsules, suspended in cornstarch or in the form of aqueous solutions or suspensions respectively. The oral dosage may range between about 0.1 and 100 mg/kg/day, preferably between 0.5 and 50 mg/kg/day and advantageously between about 0.3 and 2.5 mg/kg/day. Said compounds produce, for example, at the above oral doses, especially between about 0.1 and 5 mg/kg/day, a decrease of the leverpressing avoidance responses of squirrel monkeys. The test procedure used is the following: Monkeys were trained to press a lever to avoid the onset of an electric foot shock. Each lever press postpones the shock for 20-seconds. Whenever the monkey fails to press the lever once within a 20-second period, brief (0.5 sec.) shocks are delivered at 20-second intervals until the animal again presses the lever. Under control conditions the monkeys press the lever at a moderately steady rate and seldom receive more than five or six shocks during a 4-hour experimental session. Said compounds evaluated for neuroleptic activity, block the learned conditioned avoidance behavior, as manifested by a marked increase in the electric shocks taken by the animal. Accordingly, the compounds of the invention are useful neuroleptics, for example, in the treatment or management of aggression, agitation, autism and/or anxiety in warm-blooded animals, preferably mammals. They are also valuable antihypertensives or intermediates for other preparations, preferably pharmacologically useful products.

Preferred and highly active compounds of the invention are those of Formula I, in which $n$ is an integer from 1 to 4, and each of $R_1$ and $R_2$ is hydrogen, alkyl or alkoxy with up to 4 carbon atoms, fluorine, chlorine, bromine or trifluoromethyl, the 3,4-dehydro derivative or a therapeutically acceptable acid addition salt thereof.

Especially important neuroleptic agents are compounds of Formula I, in which $n$ is either 1 or 2, and each of $R_1$ and $R_2$ is hydrogen, methyl, ethyl, methoxy, ethoxy, fluorine, chlorine, bromine or trifluoromethyl, the 3,4-dehydro derivative or a therapeutically acceptable acid addition salt thereof.

More valuable on account of their activity are compounds of Formula I, in which $n$ is 1, $R_1$ is hydrogen, methyl, methoxy, fluorine, chlorine or trifluoromethyl and $R_2$ is hydrogen; the 3,4-dehydro derivative or a therapeutically acceptable acid addition salt thereof.

The most promising compound of the invention is the 4′-fluoro-4-[4-(α-hydroxy-α-methylbenzyl)-piperidino]-butyrophenone, especially its dextrorotatory optical isomer, or advantageously a therapeutically acceptable acid addition salt thereof, which exhibit outstanding effects in the above-described test system (Sidman procedure). For example, the dextrorotatory methanesulfonate thereof, when administered once at dosages between 0.3 and 5 mg/kg to squirrel monkeys, displays a very rapid onset of action of unusual long duration without observable neurological deficit.

The compounds of the invention are prepared according to known methods, for example, by:

a. condensing compounds of Formulae III and IV

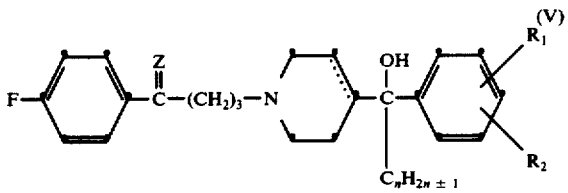

(III)    (IV)

in which Y is a reactively esterified hydroxy group or
b. hydrolyzing a compound of Formula V

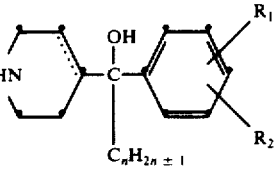

(V)

in which Z is a ketalized oxo or thiono group derived from a lower alkanediol or dithiol or a lower thioalkanol and, if desired, converting any resulting compound into another compound of the invention.

A reactively esterified hydroxy group Y, mentioned under item (a) is preferably such derived from a strong mineral acid or an aliphatic or aromatic sulfonic acid, e.g., sulfuric, methane, ethane, benzene, toluene or camphor sulfonic acid but preferably that of a hydrohalic acid, e.g., hydrobromic, hydriodic or especially hydrochloric acid.

The corresponding condensation is preferably carried out in the presence of basic agents, for example, alkali or alkaline earth metal carbonates, hydroxides, or lower alkoxides, such as sodium, potassium or calcium carbonate, sodium or potassium hydroxide, methoxide or ethoxide. Also organic nitrogen bases can be used, such as aliphatic or aromatic tertiary amines, for example tri-lower alkylamines, e.g., triethylamines; pyridine or collidine. It is also advantageous to employ a catalyst, for example, an ion in common with the condensing agents, for example, where sodium carbonate is used, a crystal of sodium halide, preferably sodium iodide, is found to enhance the reaction.

The hydrolyzing according to item (b) is carried out in the usual manner, for example in mixtures of organic and acidic aqueous mediums, especially alcoholic mineral or sulfonic acids, e.g., those mentioned above.

The compounds of the invention can be converted into each other by known methods. For example a resulting 3,4-dehydroderivative can be hydrogenated, preferably with catalytically activated hydrogen, e.g., over palladium or platinum catalysts.

The above processes are carried out according to standard methods, e.g., in the presence or absence of diluents, preferably such as are inert to the reagent and being solvents thereof, of catalysts, condensing or reducing agents respectively and/or inert atmospheres, at low temperatures, room temperature or elevated temperatures, at atmospheric or superatmospheric pressure.

Solvents employed in the condensation reaction according to item (a), are preferably polar solvents, such as alcohols or ketones, for example, lower alkanols or simple or mixed lower alkanones, such as methanol, ethanol; acetone, 2-butanone or, above all, 4-methyl-2-pentanone. Also useful are polar aprotic solvents, such as lower alkanonic acid amides or dilower alkylsulfoxides, e.g., dimethylformamide, dimethyeacetamide or dimethylsulfoxide.

The compounds of the invention are obtained in the free form or in the form of their salts, depending on the conditions under which the process is carried out; the salts are also included in the present invention. Salts that are obtained can be converted into the free bases in known manner, for example, with alkalies or ion exchangers. Free bases that are obtained can be converted into salts by reaction with inorganic or organic acids, especially those that are suitable for the formation of therapeutically acceptable salts. Such acids are, for example, mineral acids, e.g., hydrochloric, hydrobromic, sulfuric, phosphoric, nitric or perchloric acid; aliphatic or aromatic carboxylic or sulfonic acids, e.g., formic, acetic, propionic, succinic, glycollic, lactic, malic, tartaric, citric, ascorbic, maleic, hydroxymaleic, pyruvic, phenylacetic, benzoic, 4-aminobenzoic, anthranilic, 4-hydroxybenzoic, salicylic, 4-aminosalicylic, embonic, nicotinic, methanesulfonic, ethanesulfonic, hydroxyethanesulfonic, ethylenesulfonic, halogenbenzenesulfonic, toluenesulfonic, naphthalenesulfonic, sulfanilic or cyclohexylsulfamic acid; methionine, tryptophan, lysine or arginine.

These or other salts of the invention, for example, the picrates, can also be used for purification of the bases obtained; the bases are converted into salts, the salts are separated and the bases are liberated from the salts. In view of the close relationship between the free compounds and the compounds in the form of their salts, whenever a free base is referred to in this context, a corresponding salt is also intended, provided such is possible or appropriate under the circumstances.

The invention further includes any variant of the present process, in which an intermediate product obtainable at any stage of the process is used as starting material and any remaining steps are carried out, or the process is discontinued at any stage thereof, or in which the starting materials are formed under the reaction conditions, or in which the reaction components are used in the form of their salts. Mainly, those starting materials should be used in the process of the invention that lead to the formation of those compounds indicated above as being specially valuable.

The starting materials are known, or if new, may be prepared according to known methods illustrated by the Examples herein, or the literature cited. Under item (a), reactively converted 4'-fluoro-4-hydroxybutyrophenones are either commercially available, e.g., 4'-fluoro-4-chlorobutyrophenone, or readily prepared by the Friedel-Crafts reaction on fluorobenzene with a reactively converted 4-hydroxybutyryl chloride in the presence of a Lewis acid, for example, aluminum chloride. The other reactant, i.e., the 4-(α-hydroxy-aralkyl)-piperidine, is advantageously prepared by two alternate synthetic routes, depending on the substituents on the phenyl ring. When substituents $R_1$ and $R_2$ are not sensitive to hydrogenation, said piperidines are obtained by hydrogenation of the corresponding pyridines; it is preferably carried out catalytically in an inert solvent, or preferably in an aqueous acidic medium, such as aqueous acetic acid. The catalyst employed is preferably palladium on charcoal support. The pyridines in turn are prepared by the treatment of readily available 4-aroylpyridines with a corresponding aliphatic or cycloaliphatic metallic reagent and hydrolysis of the resulting adduct. This reaction involves preferably the addition of a lower alkyl magnesium halide to the carbonyl compound and hydrolysis of the reaction product with aqueous acidic reagents, to afford the pyridine-carbinols.

In case said 4-(α-hydroxyaralkyl)-piperidines contain substituents $R_1$ and $R_2$ sensitive to hydrogenation, they can be prepared by the addition of said metallic reagents to corresponding N-acyl-4-aroylpiperidines in the manner described above. The starting N-acyl-4-aroylpiperidines are prepared essentially as described in U.S. Pat. No. 3,576,810.

The starting material used under item (b) is prepared as follows, employing similar reaction conditions as already described. A reactively converted 4'-fluoro-4-hydroxybutyrophenone is initially ketalized, e.g., treated with ethylene glycol or β-mercaptoethanol, in the presence of an acidic catalyst, to form the 1,3-dixolane or 1,3-oxathiolane thereof. This reaction is advantageously carried out in the presence of an inert solvent and one immiscible with water, in order to remove the water formed in the ketalization. The reaction is thus especially carried out at reflux temperatures in solvents such as aromatic hydrocarbons, for example, benzene, toluene or xylene. The water formed is removed by means of an azeotropic distillation trap. The acid catalyst employed is normally a sulfonic acid, for example, p-toluenesulfonic acid, but can also be a Lewis acid or a mineral acid, such as zinc chloride, boron trifluoride, hydrochloric or sulfuric acid. The resulting dioxolane or oxathiolane is then condensed in a similar manner described in the reaction under item (a) with a 4-aroyl-piperidine, obtained as described in U.S. Pat. No. 3,576,810. The resulting condensation product is treated with a Grignard reagent, as described above, and hydrolyzed to form the starting material under item (b).

Starting materials or final products that are mixtures of isomers can be separated into the single isomers by methods in themselves known, e.g. by fractional distillation, crystallization and/or chromatography. Racemic products can likewise be resolved into the optical antipodes, for example, by separation of diastereomeric salts or esters thereof, e.g., by the fractional crystallization fo d- or l- tartrates, -maleates, -malates -N-acetyl-phenylalaninates or-camphorsulfonates, and re-converting the diastereomeric salts or esters into the free antipodes, or using said ester intermediates direct in reaction (a). Thus, for example, compounds of Formula I are converted into their individual optical isomers, preferably by treatment with d- or l-tartaric acid. The resulting diastereoisomeric salt is recrystallized and reconverted to the free antipode. The reconversion is carried out by hydrolysis with, for example, a basic agent, such as an alkali metal hydroxide, e.g., sodium or potassium hydroxide, or ammonium hydroxide. A more preferred embodiment involves the direct preparation of dextro- or levorotatory isomers of the compounds of Formula I by the processes described under items (a) and (b), from their optically active starting materials. Thus, for example, starting materials under item (b) can be resolved as described above for the final product. Under item (a), the piperidine starting materials are resolved essentially as described above with preferably d- or l-tartaric acid. The free antipodes thereof are condensed as indicated under item (a) to form the corresponding dextro- or levorotatory isomers of the compounds of Formula I. For example, treatment of a racemic pyridine-methanol compound under item (a) with l-tartaric acid in an alcoholic solution at preferably elevated temperatures will afford on cooling the crystalline 1-diastereoisomeric salt. The salt is recrystallized and hydrolyzed in an aqueous solution with, for example, an alkali metal hydroxide, e.g., sodium hydroxide. The free antipode is recrystallized to a constant rotation and is the dextorotatory isomer. Condensation of this dextrorotatory isomer with the butyrophenone under item (a) affords the dextrorotatory compound of Formula I. Correspondingly, when the d, 1 -piperidine is treated with d-tartaric acid, the 1 -piperidine is obtained, which, when reacted with the butyrophenone, results in the levorotatory form of the compounds of Formula I, which are more useful as antihypertensive agents.

The pharmacologically active compounds of the invention are useful in the manufacture of pharmaceutical compositions comprising an effective amount thereof in conjunction or admixture with excipients suitable for either enteral or parenteral application. Preferred are tablets and gelatin capsules comprising the active ingredient together with (a) diluents, e.g., lactose, dextrose, sucrose, mannitol, sorbitol, cellulose and/or glycine, (b) lubricants, e.g., silica, talcum, stearic acid, its magnesium or calcium salt and/or polyethyleneglycol, for tablets also (c) binders, e.g., magnesium aluminum silicate, starch paste, gelatin, tragacanth, methylcellulose, sodium carboxymethylcellulose and/or polyvinylpyrrolidone, if desired, (d) disintegrants, e.g., starches, agar, alginic acid or its sodium salt, enzymes of the binders or effervescent mixtures and/or (e) absorbents, colorants, flavors and sweeteners. Injectable compositions are preferably aqueous isotonic solutions or suspensions, and suppositories are advantageously fatty emulsions or suspensions. They may be sterilized and/or contain adjuvants, such as preserving, stabilizing, wetting or emulsifying agents, solution promoters, salts for regulating the osmotic pressure and/or buffers. Said pharmaceutical compositions may also contain other therapeutically valuable substances. They are prepared according to conventional mixing, granulating or coating methods respectively and contain about 0.1 to 75%, preferably about 1 to 50%, of the active ingredient.

The following examples are intended to illustrate the invention and are not to be construed as being limitations thereon. Temperatures are given in degrees centigrade, and all parts wherever given are parts by weight.

EXAMPLE 1

The mixture of 2 g of α-methyl-α-(4-piperidyl)-benzyl alcohol, 1.95 g of 4'-fluoro-4-chlorobutyrophenone, 2 g of sodium carbonate (anhydrous), a crystal of sodium iodide and 150 ml of 4-methyl-2-pentanone are stirred and refluxed for 72 hours. The reaction mixture is filtered to remove the inorganic salts and the filtrate evaporated under reduced pressure. Diethyl ether is added to the residue and the resulting solution extracted with 5% aqueous hydrochloric acid. The aqueous solution is made basic with ammonia and extracted with diethyl ether. The extract is then dried and evaporated under reduced pressure to afford the 4'-fluoro-4-[4-(α-hydroxy-α-methylbenzyl)-piperidino]- butyrophenone of the formula

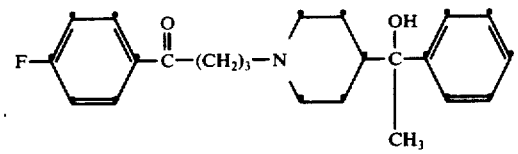

Recrystallization from isopropanol yields the above compound melting at 55°-57° and isolated as a solvate.

The starting α-methyl-α-(4-piperidyl)-benzyl alcohol is prepared as follows:

To the mixture of 6.6 g of magnesium and 50 ml of diethyl ether is added dropwise 40 g of methyl iodide in 300 ml of diethyl ether. The resulting mixture is refluxed for 30 minutes, followed by the addition of 25 g of 4-benzoylpryridine in 75 ml of tetrahydrofuran, added dropwise. The total reaction mixture is then refluxed for 4 hours, cooled and treated with 50 ml of saturated ammonium chloride, added dropwise. The solvents from the mixture are decanted and 800 ml of chloroform is added to the semi-solid residue. The resulting chloroform solution is heated on a steam bath, filtered, and the filtrate evaporated under reduced pressure. The crude material obtained is recrystallized from ethanol to yield the α-methyl-α-(4-pyridyl)-benzyl alcohol, melting at 141°-144°.

The mixture of 18 g of the above benzyl alcohol, 180 ml of glacial acetic acid, 20 ml of water and 9 of 10% palladium on charcoal is treated with hydrogen at 60 p.s.i. and room temperature. Following the theoretical uptake of hydrogen, the reaction mixture is filtered to remove the catalyst. The filtrate is evaporated under reduced pressure and the residue treated with 50% aqueous sodium hydroxide. The resulting mixture is extracted with chloroform; the chloroform extract is dried and evaporated under reduced pressure to yield the α-methyl-α-(4-piperidyl)-benzyl alcohol, melting at 172°-175°.

EXAMPLE 2

The mixture of 2.5 g of α-methyl-α-(4-piperidyl)-p-chlorobenzyl alcohol, 2.08 g of 4'-fluoro-4-chlorobutyrophenone, 2.5 g of sodium carbonate, a crystal of sodium iodide and 120 ml of 4-methyl-2-pentanone, is stirred and refluxed for 72 hours. The reaction mixture is worked up in usual manner as described in the previous example. The product is finally isolated as described above in the form of an oil and is the 4'-fluoro-4-[4-(α-hydroxy-α-methyl-p-chlorobenzyl)-piperidino]-butyrophenone.

The above compound as an oil is taken up in absolute etnahol and treated with hydrogen bromide until acidic and precipitation is complete. The solids are collected on the filter affording the hydrobromide salt of the above compound, melting at 168°-170° with decomposition.

The starting α-methyl-α-(4-piperidyl)-p-chlorobenzyl alcohol is prepared as follows:

The mixture of 100 g of isonipecotic acid and 40 ml of acetic anyhydride is refluxed for 2 hours and then allowed to stir at room temperature overnight. The reaction mixture is then evaporated under reduced pressure and the residue triturated with diethyl ether. The resulting solids are recrystallized from a mixture of isopropanol and diethyl ether to afford the N-acetyl isonipectic acid, melting at 175°.

58 g thereof is added to 400 ml of thionylchloride. The resulting solution is stirred at room temperature for 5 hours during which time solids are formed. The mixture is poured into 1 l of petroleum ether (30°-60°); the resulting solution filtered, washed and dried to afford the N-acetylisonipecotic acid chloride.

36 g thereof added gradually to a suspension of 47.5 g of aluminum chloride in 80 ml of cholorbenzene. The reaction mixture is refluxed for 1 hour and poured cautiously onto ice. The organic layer is separated and the aqueous layer washed with chloroform. The combined organic extracts are dried and evaporated under reduced pressure. The solid residue is recyrstallized from a mixture of benzene and petroleum ether (30°-60°) affording the N-acetyl-4-piperidyl-p-chlorophenyl ketone of the formula

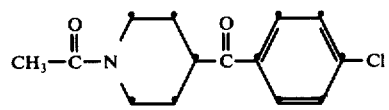

The mixture of 10 g thereof and 100 ml of tetrahydrofuran diethyl ether (3:1) is added dropwise to a solution of methylmagnesium iodide prepared from 5 g of magnesium and 28.4 g of methyl iodide and 40 ml of diethyl ether. The reaction mixture is refluxed for 4 hours and then decomposed with 36 ml of saturated aqueous ammonium chloride solution. The solvents are evaporated under reduced pressure and the inorganic salts remaining are dissolved in 5% aqueous hydrochloric acid. The acid solution is extracted with methylene chloride. The organic extract is then dried and evaporated to give the α-methyl-α-(N-acetyl-4-piperidyl)-p-chlorobenzyl alcohol.

2.9 g thereof is hydrolyzed with 3 g of potassium hydroxide in 6 ml of water and 24 ml of ethanol overnight on a steam bath. The solvent is then evaporated and the residue diluted with diethyl ether. The ether solution is extracted with 5% aqueous hydrochloric acid. The aqueous acid solution is made basic with ammonia and the organic base extracted with methylene chloride. The organic extract is dried and evaporated to afford a solid which when recrystallized from ethanol yields the α-methyl-α-(4-piperidyl)-p-chlorobenzyl alcohol, melting at 178°-180°.

EXAMPLE 3

The mixture of 2 g of 1-α-methyl-α-(4-piperidyl)-benzyl alcohol, 1.95 g of 4-chloro-4'-fluorobutyrophenone, 2 g of sodium carbonate, a crystal of sodium iodide and 150 ml of 4-methyl-2-pentanone is stirred at reflux for 72 hours. The reaction mixture is worked up as described in Example 1 to afford the 1-4'-fluoro-4-[4-(α-hydroxy-α-methylbenzyl)-piperidino]-butyrophenone, which when recrystallized from isopropanol and dried at 50° in vacuum has a specific rotation of $[\alpha]_D^{25} = -15.8°$ (CHCl$_3$), melting at 75°-78°.

The use of 2 g of d-α-methyl-α-(4-piperidyl)-benzyl alcohol in the above reaction gives the corresponding d-4'-fluoro-4-[4-(α-hydroxy-α-methylbenzyl)-piperidino]-butyrophenone, which when recrystallized from isopropanol and dried at 50° in vacuum melts at 75°-78° and has a specific rotation of $[\alpha]_D^{25} = +15.8°$ (CHCl$_3$).

The starting 1-α-methyl-α-(4-piperidyl)-benzyl alcohol is prepared as follows:

The mixture of d,l-α-methyl-α-(4-piperidyl)-benzyl alcohol, 50 ml of absolute ethanol and 2.9 g of d-tartaric acid is heated to reflux. On cooling, crystals form which are collected on a filter and then recrystallized from 95% ethanol to give the dl-diastereoisomeric salt. The salt is dissolved in 20 ml of water and made strongly alkaline with sodium hydroxide. The resulting mixture is extracted with methylene chloride. The organic layer is then washed, dried and evaporated under reduced pressure affording the 1-α-methyl-α-(4-piperidyl)-benzyl alcohol, melting at 164°-165° and having a specific rotation $[\alpha]_D^{25} = -30°$ (CHCl$_3$).

Employing l-tartaric acid in the above reaction affords the d-α-methyl-α-(4-piperidyl)-benzyl alcohol, melting at 164°-165° and having a specific rotation of $[\alpha]_D^{25} = +30°$ (CHCl$_3$).

EXAMPLE 4

A mixture of 2.7 g of 4-chloro-4'-fluorobutyrophenone, 2.5 g of α-methyl-α-(4-piperidyl)-p-fluorobenzyl alcohol, 8 g of sodium carbonate, a crystal of sodium iodide and 30 ml of 4-methyl-2-pentanone is stirred and refluxed for 72 hours. The reaction mixture is worked up in the usual manner as described in the previous Examples. The product is isolated as described above and recrystallized from isopropanol to afford the 4'-fluro-4-[4-(α-hydroxy-α-methyl-p-fluorobenzyl)-piperidino]-butyrophenone, melting at 116°-118°.

The corresponding d-isomer is obtained as described in Example 3 from the d-α-methyl-α-(4-piperidyl)-p-fluorobenzyl alcohol and melts at 112°-115° having a specific rotation of $[\alpha]_D^{25} = +14°$ (CHCl$_3$).

The starting α-methyl-α-(4-piperidyl)-p-fluorobenzyl alcohol is prepared as follows:

To the mixture of 4.8 g of magnesium, covered with 30 ml of anyhydrous diethyl ether, is added dropwise 35 g of p-bromo-fluorobenzene in 150 ml of anhydrous diethyl ether. The resulting mixture is refluxed for approximately 1 hour, cooled, and there is subsequently added dropwise 25 g of 4-acetylpyridine in 50 ml of diethyl ether. Solids are formed immediately on the addition. The total reaction mixture is stirred and refluxed for 3 hours, cooled and treated with 36 ml of saturated aqueous ammonium chloride. The precipitate is filtered and extracted by refluxing with chloroform. The filtrate is evaporated under reduced pressure and the residue recrystallized from ethanol to afford the α-methyl-α-(4-pyridyl)-p-flurorobenzyl alcohol, melting at 160°-162°.

The mixture of 10 g thereof, 10 g of 10% palladium on charcoal, 225 ml of glacial acetic acid and 25 ml of water is treated with hydrogen at 4.8 atm. at room temperature. Following the theoretical uptake of hydrogen, the reaction mixture is filtered to remove the catalyst. The filtrate is evaporated under reduced pressure and the residue treated with 50% aqueous sodium hydroxide. The resulting base is crystallized and collected on the filter, washed with water and recrystallized from ethanol to yield the α-methyl-α-(4-piperidyl)-p-fluorobenzyl alcohol, melting at 184°-186°.

The corresponding d-isomer is obtained as described in Example 3 and has a specific rotation of $[\alpha]_D^{25} = +24.1°$ (CHCl$_3$).

EXAMPLE 5

A mixture of 2.0 g of 4-(α-hydroxy-α-methyl-4-fluorobenzyl)-1,2,5,6-tetrahydropyridine, 2.5 g of 4'-fluoro-4-chlorobutyrophenone, 3.0 g of sodium carbonate, a crystal of sodium iodide, in 100 ml of 4-methyl-2-pentanone is stirred and refluxed for 72 hours. It is cooled, filtered, and the filtrate evaporated under reduced pressure. Diethyl ether is added to the residue and the resulting solution extracted with 5% aqueous hydrochloric acid. The aqueous solution is made basic with ammonium hydroxide and extracted with diethyl ether. The extract is dried, evaporated and the residue recrystallized from isopropanol, to give the 4'-fluoro-4-[4-(α-hydroxy-α-methyl-4-fluorobenzyl)-1,2,5,6-tetrahydropyridyl]-butyrophenone melting at 95°.

The starting material is prepared as follows: A mixture of 15 g of 4-(α-hydroxy-α-methyl-4-fluorobenzyl)-pyridine, 8.2 ml of benzyl bromide and 100 ml of acetonitrile is refluxed overnight. The solvent is evaporated and the residue recrystallized from isopropanol-diethyl ether, to yield the desired 1-benzyl-4-(α-hydroxy-α-methyl-4-fluorobenzyl)-pyridinium bromide melting at 175° with decomposition.

To a solution of 20 g thereof in 100 ml of methanol, 20 g of sodium borohydride are added slowly while stirring and cooling with ice. After stirring over night at room temperature the mixture is filtered and the residue recrystallized from aqueous methanol, to yield the 1-benzyl-4-(α-hydroxy-α-methyl-4-fluorobenzyl)-1,2,5,6-tetrahydropyridine. A solution of 3 g thereof in 50 ml of ethanol-water (1:1) and 18 ml of concentrated hydrochloric acid is hydrogenated over 0.5 g of 10% palladium on carbon at 2.7 atm. until one molar equivalent of hydrogen has been absorbed. It is filtered, the filtrate concentrated to a small volume, the concentrate made basic with aqueous sodium hydroxide and extracted with chloroform. The extract is dryed, evaporation and the residue recrystallized from isopropanol, to yield the 4-(α-hydroxy-α-methyl-4-fluorobenzyl)-1,2,5,6-tetrahydropyridine melting at 168°.

EXAMPLE 6

A mixture of 3.0 g of 4-(α-hydroxy-α-methyl-p-chloro-m-trifluoromethylbenzyl)-piperidine, 3.0 g of 4'-fluoro-4-chlorobutyrophenone, 3.0 g of sodium carbonate, a crystal of sodium iodide and 200 ml of 4-methyl-2-pentanone, is stirred and refluxed for 72 hours. The reaction mixture is worked up in the usual manner as described in the previous examples. The product is finally isolated as a foam and is the 4'-fluoro-4-[4-(α-hydroxy-αmethyl-p-chloro-m-trifluoromethylbenzyl)-piperidino]-butyrophenone.

The starting material 4-(α-hydroxy-α-methyl-p-chloro-m-dtrifluoromethylbenzyl)-piperidine is prepared in the usual manner described in the other examples by reacting a Grignard reagent of p-chloro-m-trifluoromethyl phenyl magnesium bromide with 4-acetylpyridine and the resulting product which is α-methyl-α-(4-pyridyl)-p-chloro-m-trifluoromethylbenzyl alcohol reduced with hydrogen using platinum oxide as the catalyst to give the starting material. The hydrochloride salt of the starting material is prepared in the usual manner and has a melting point of 128°-130°.

EXAMPLE 7

The compound 4'-fluoro-4-[4-(α-hydroxy-α-methyl-m-trifluoromethylbenzyl)-piperidino]-butyrophenone is prepared according to Example 6 except that 3-bromobenzotrifluoride is used to react with magnesium turnings to prepare the usual Grignard reagent.

EXAMPLE 8

Preparation of 10,000 tablets each containing 1.0 mg of the drug substance:

| Formula: | |
|---|---|
| d-4'-fluoro-4-[4-(α-hydroxy-α-methylbenzyl)-piperidino]-butyrophone methanesulphonate | 10.00 g |
| Lactose | 828.00 g |
| Corn Starch | 50.00 g |
| Polyethylene glycol 6,000 | 50.00 g |
| Talcum Powder | 50.00 g |
| Magnesium stearate | 12.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 25 ml of water and the suspension added to the boiling solution of the polyethylene glycol in 100 ml of water. The paste formed is added to the powders which are granulated, if necessary, with an additional amount of water. The granulate is dried overnight at 35°, broken on a screen with 1.2 mm openings and compressed into tablets using flat punches with 4.8 mm diameter, uppers bisected.

I claim:

1. The 4'-fluoro-4[4-(α-hydroxy-α-methylbenzyl)-piperidino]-butyrophenone, or a therapeutically acceptable acid addition salt thereof.

2. A compound as claimed in claim 1 and being the dextrorotatory 4'-fluoro-4-[4-(α-hydroxy-α-methylbenzyl)-piperidino]-butyrophenone, or a therapeutically acceptable acid addition salt thereof.

3. A compound as claimed in claim 1 and being the dextrorotatory methanesulfonate of the 4'-fluroro-4-[4-(α-hydroxy-α-methylbenzyl)-piperidino]-butyrophenone.

* * * * *